(12) United States Patent
Poynot

(10) Patent No.: US 6,332,349 B1
(45) Date of Patent: Dec. 25, 2001

(54) INSTALLATION FOR ANALYZING AN ATMOSPHERE

(75) Inventor: Philippe Poynot, Gif sur Yvette (FR)

(73) Assignee: L'Air Liquide, Societe Anonyme pour l'Etude et l'Exploitation des procedes Georges Claude, Paris (FR)

( * ) Notice: Subject to any disclaimer, the term of this patent is extended or adjusted under 35 U.S.C. 154(b) by 0 days.

(21) Appl. No.: 09/327,518

(22) Filed: Jun. 8, 1999

(30) Foreign Application Priority Data

Jun. 15, 1998 (FR) .................................. 98 07498

(51) Int. Cl.⁷ .............................. G01N 1/26; G01N 35/00
(52) U.S. Cl. ..................... 73/23.2; 73/863.31; 73/863.33
(58) Field of Search ............................... 73/23.2, 31.05, 73/863.31, 863.33

(56) References Cited

U.S. PATENT DOCUMENTS

| | | | |
|---|---|---|---|
| 3,069,898 | 12/1962 | Vesper | 73/23.42 |
| 3,357,257 | * 12/1967 | Herndon et al. | 73/863.33 |
| 3,369,405 | * 2/1968 | Galegar | 73/863.33 |
| 3,921,457 | 11/1975 | Barnes, Jr. et al. | 73/863.33 |
| 4,090,392 | 5/1978 | Smith et al. | 73/863.33 |

FOREIGN PATENT DOCUMENTS

| | | | |
|---|---|---|---|
| 181580 | 5/1936 | (CH) . | |
| 19607574 | 9/1997 | (DE) . | |
| 476674 | 3/1992 | (EP) | 73/863.33 |
| 579055 | 1/1994 | (EP) . | |
| 996361 | 3/1964 | (GB) | 73/863.33 |

* cited by examiner

Primary Examiner—Daniel S. Larkin

(74) Attorney, Agent, or Firm—Burns, Doane, Swecker & Mathis, L.L.P.

(57) ABSTRACT

Installation for analyzing the level of at least one element, from at least two initial gas sources ($S_1$, $S_2$, ...) in a sampling procedure, using at least one analyzer ($A_1$, $A_2$, ...) capable of analyzing the element, including:

- at least two sources ($S_1$, $S_2$, ...) of initial gases to be analyzed;
- at least two tapping lines ($L_{p1}$, $L_{p2}$, ...), each line being connected in its upstream part to one of the initial gas sources, and in its downstream part to a respective flow-directing component ($V_1$, $V_2$, ...);
- at least two discharge lines ($L_{E1}$, $L_{E2}$, ...), each discharge line being connected in its upstream part to one of the directing components and in its downstream part to a discharge or to a storage point ($E_1$, $E_2$, ...);
- at least two secondary lines ($L_{s1}$, $L_{s2}$, ...), each secondary line being connected in its upstream part to one of the directing components and, in its downstream part, to a collection point (R), each directing component being capable of directing a sample from the initial gas source which is associated with it to its respective discharge line or to the collection point via its respective secondary line;
- a tertiary line ($L_T$), connected in its upstream part to the collection point and in its downstream part to a discharge or to a storage point (E);
- at least one analysis line ($L_{Ai}$), connected in its upstream part to the tertiary line and in its downstream part to at least one of the at least one analyzers.

15 Claims, 3 Drawing Sheets

INSTALLATION FOR ANALYZING AN ATMOSPHERE

BACKGROUND OF THE INVENTION (i) Field of the Invention

The present invention relates to the field of atmospheric analysis equipment, and quite particularly deals with the case in which it is necessary to analyze one or more elements of an atmosphere at a plurality of points of an enclosure employing this atmosphere, or of a gas distribution network, this being in multiplexing mode (batch mode: sequential analysis of the points in an order which may be varied and with an addressing time for each measurement point which can also be varied).

(ii) Description of Related Art

These analysis applications fall within a context in which users of industrial gases (heat treatment, electronics, food, etc.) increasingly frequently need to analyze one or more components of the atmosphere which they are employing in a given user station, or alternatively one or more impurities (such as oxygen or alternatively water vapor) of a distributed gas before it is injected into their process, this being so as to be capable of carrying out comprehensive quality control on the articles being processed, this comprehensive quality control presupposing that it is possible to know the atmospheric conditions under which each article has been processed.

Customers using gases therefore often wish to be able to know these atmospheric conditions, or to display and archive them, with trackability, or even to process these values thus archived.

It can therefore be seen that the possibility should be available of providing these customers, who use industrial gases, with analysis methods and equipment allowing gas samples to be taken at the various analysis points which are monitored (whether these are various points of an enclosure employing the atmosphere for a given treatment, or various analysis points on a gas distribution network), making it possible:

to minimize the response time of the analyzer or analyzers in question;

to ensure that the analysis bay is provided with samples of gas to be analyzed which are representative of the atmosphere of the enclosure or of the gas flowing in the distribution network to be analyzed, and in particular, as will be understood, in the case when the analysis bay is far away from the tapping points;

to take samples and carry out analyses irrespective of the order of each measurement point;

to take samples and carry out analyses whatever the addressing time of a given measurement point, depending on the species analysed and the type of analyzer employed.

For such multiplexing applications, it has been proposed to use rotary valves based on stepwise advance of the valve, which becomes positioned in turn in front of each channel to be analysed. The use of such rotary valves is not, however, without its drawbacks, in particular linked with complex hardware, whose operational robustness remains to be proven, but above all for which a very precise rotational advance order needs to be adhered to.

SUMMARY AND OBJECTS OF THE INVENTION

The object of the present invention is in particular to provide solutions to the technical problems mentioned above.

The installation for analyzing the level of at least one element, from at least two initial gas sources, according to a sampling procedure, using at least one analyzer capable of analyzing the said element, according to the invention then includes:

at least two sources of initial gases to be analyzed;

at least two tapping lines, each line being connected in its upstream part to one of the initial gas sources, and in its downstream part to a respective flow-directing component;

at least two discharge lines, each discharge line being connected in its upstream part to one of the directing components and in its downstream part to a discharge or to a storage point;

at least two secondary lines, each secondary line being connected in its upstream part to one of the directing components and, in its downstream part, to a collecting point, each directing component being capable of directing a sample from the initial gas source which is associated with it to its respective discharge line or to the collection point via its respective secondary line;

a tertiary line, connected in its upstream part to the collection point and in its downstream part to a discharge or to a storage point;

at least one analysis line, connected in its upstream part to the tertiary line and in its downstream part to at least one of the at least one analyzers.

The analysis installation according to the invention may moreover have one or more of the following characteristics:

a pumping component, located between the collection point and the point of connection between analysis line and tertiary line;

the tertiary line includes a non-return valve downstream of the point of connection of the analysis line to the tertiary line;

the tertiary line includes an overflow downstream of the point of connection of the analysis line to the tertiary line, and the analysis line or at least one of the analysis lines is provided with a component for creating a pressure head loss;

the discharge line or at least one of the discharge lines is provided with a pumping component;

the or each analysis line is provided with a directing component which makes it possible, depending on the case, to direct a calibration gas or a purging gas to the analyzer of the gas to be analysed;

the directing component or components consist of a three-way solenoid valve;

the directing component or components of the tapping lines consist of the assembly formed by the point of connection of the associated tapping, discharge and secondary lines, each secondary and discharge line being provided, downstream of this point, with a component capable of allowing or interrupting the flow of gas through the line in question;

the initial sources to be analyzed are at a pressure above atmospheric pressure;

the initial sources to be analyzed are at a pressure substantially equal to atmospheric pressure or below atmospheric pressures;

the initial sources consist of gas samples taken from a distribution network;

the initial sources consist of gas samples taken from various points of an enclosure employing a gas atmosphere;

the installation includes a plurality of analyzers, the analysis lines being connected to the tertiary line at a feed tank;

the installation includes a single analysis line connecting the tertiary line and the analyzers arranged in series;

the installation includes one analysis line per analyzer.

Other characteristics and advantages of the present invention will emerge from the following description of embodiments which is given by way of illustration but without implying any limitation and in conjunction with the appended drawings.

DETAILED DESCRIPTION OF PREFERRED EMBODIMENTS

Figure 1:
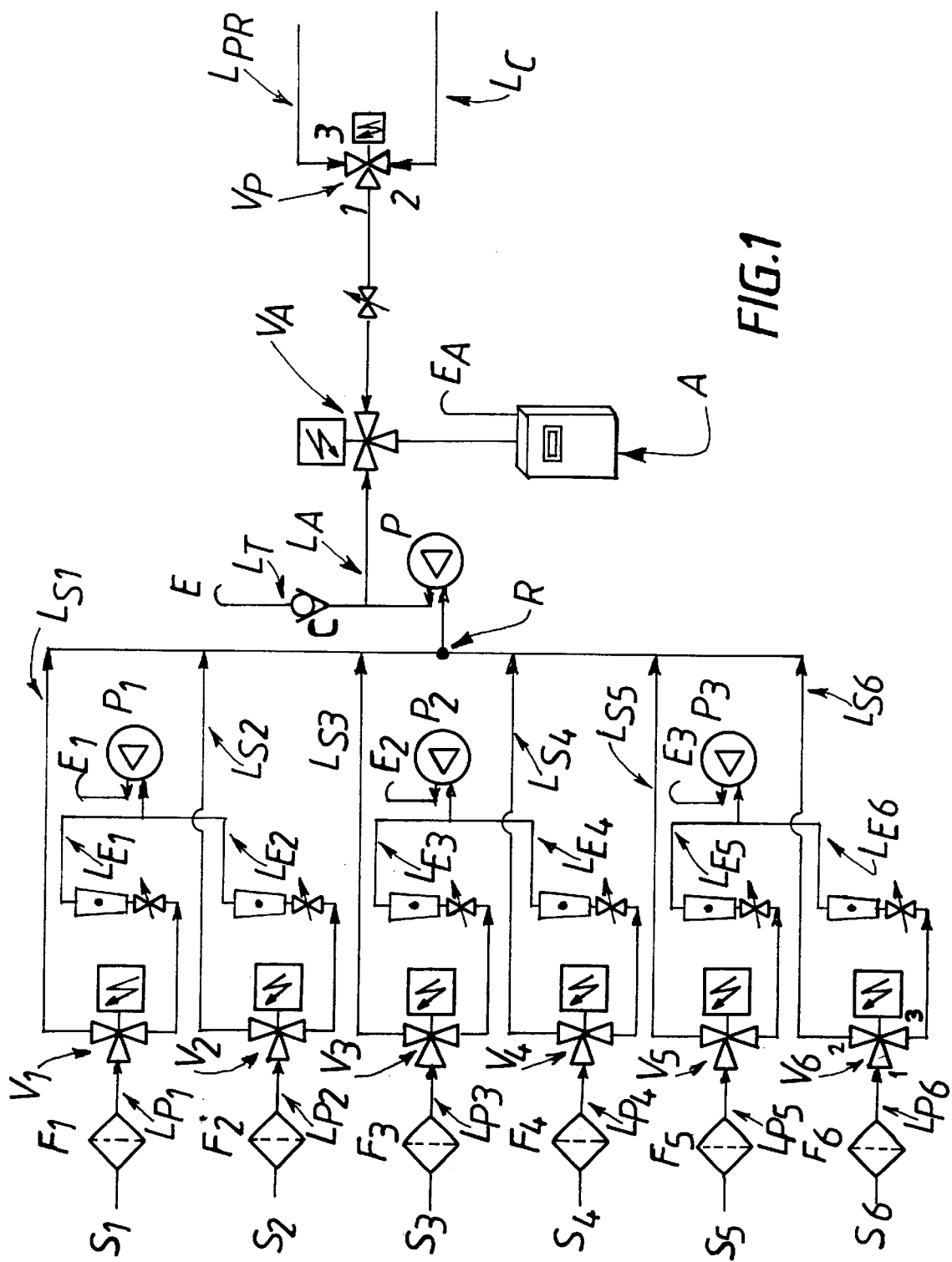
FIG. 1 is a schematic representation of an installation according to the invention, employing a single analysis line and a single analyser.

FIG. 1 is a schematic representation of an installation according to the invention, including six tapping lines $L_{pi}$, each starting from an initial gas source $S_i$, each tapping line being connected to a flow-directing component $V_i$, here, in each case, a three-way solenoid valve, by passing through a filter $F_i$.

The initial sources may for example consist of gas samples taken from a distribution network (a typical application of monitoring impurities before authorizing introduction into a process), or alternatively, for example, may consist of gas samples taken at various points of an enclosure employing a gas atmosphere (furnace, tunnel, storage container, etc.).

The initial sources to be analyzed are then, depending on the case, at a pressure above atmospheric pressure (which is the case with distribution networks in which several bar, or even tens of bar may be reached), or alternatively at a pressure substantially equal to atmospheric pressure or below atmospheric pressure. It is known, for example, that in many enclosures employing industrial gases, such as heat treatment furnaces or tunnels for processing food products, the pressure inside such "open" enclosures is equal to atmospheric pressure to within a few millibar (P=PA+(1 to 50 mbar)).

According to the invention, a secondary line $L_{si}$ (which joins a collection point R), and a discharge line $L_{Ei}$, which in the embodiment represented joins a vent $E_i$, through a pumping component $P_i$, are connected to each three-way solenoid valve $V_i$.

As will have been noted, in the embodiment represented, two discharge lines have been combined on one vent, for example discharge lines one and two at one vent $E_1$, the installation with six lines which have been represented then including only three discharge vents $E_1$, $E_2$, and $E_3$.

Continuing the description of the installation in FIG. 1 downline, it can be seen that a tertiary line $L_T$, starting from the collection point R, is capable of discharging gas to a vent E, by passing through a pumping component P and a non-return valve C.

An analysis line $L_A$, capable of sending gas to be analysed to an analyzer A, by passing through a three-way solenoid valve $V_A$, is taken off from this tertiary line.

The analyzer A is also provided with a gas outlet which can discharge the received gas to a vent $E_A$.

It will furthermore be noted that the plant is supplemented by a three-way solenoid valve $V_P$, the solenoid valves $V_A$ and $V_P$ in combination making it possible, depending on the case, to direct gas to be analyzed (along the line $L_A$), calibration gas (taken from the line $L_C$), or, alternatively, a purging gas (taken from the line $L_{PR}$) to the analyzer A.

The numbers 1, 2 and 3 have been used to denote the three ways of the solenoid valve $V_6$, so as to describe its operation more conveniently, and, generally, the way in which the installation in FIG. 1 operates.

When the coil of the solenoid valve $V_6$ is on, the passage 1-2 is employed, that is to say the gas taken from the source $S_6$ is sent to the collection point R. However, when the coil of the solenoid valve $V_6$ is off, the passage 1-3 is then employed, in order to send the gas taken from the source $S_6$ to the discharge $E_3$ along the discharge line $L_{E6}$.

It can therefore be seen that the installation for multiplex-mode analysis in FIG. 1 makes it possible to take gas samples at six different points and distribute them to the analyzer, the design of the installation making it possible, using a monitoring/control system which has not been represented in the figure (such as an automation unit), to tap the various analyzed points continuously, by directing a given gas source to the analyzer A, through the collection point R, while all the other gas samples taken from the sources $S_i$ are directed to the discharges $E_i$, and so forth, the source which was previously undergoing analysis then being directed to its discharge while the solenoid valve of another source is now activated to carry out its analysis, leaving the others intact, that is to say directed to the discharges.

An installation of this type then makes it possible to tap the six initial gas sources continuously, minimizing the response time of the analyzer, and guaranteeing that this analyzer receives gas samples representative of the atmosphere at the sources $S_i$, in particular in the case when the analyzer is, for some reason or another, very far away from the tapping points.

It can also be seen that an installation of this type makes it possible to change from one initial gas source to another, in any order, and the addressing time for each measurement point is fully configurable, using a control system already mentioned above, making it possible for example to monitor certain measurement points more closely when they are for example more critical.

Similarly, in order to meet the expectations of certain users who wish to view or archive certain data (for example the time profile of the level of a given element in the atmosphere of their processing enclosure), it is easy to use the installation according to the invention by recovering, for display or storage purposes, signals taken from the analyzer or analyzers of the installation. These signals can also be processed in order, if necessary, to trigger alarms according to one or more detected levels, or, alternatively, to use the automation unit, on the basis of them, to regulate the level of one or more gas elements.

Let us consider here, as an example, the case when the initial gas sources $S_i$ are tapping points on one or more enclosures for employing industrial gases, for example, furnaces for heat treatment under controlled atmosphere, the gases in these enclosures being substantially at atmospheric pressure.

Let us then, moreover, also consider the example of the case when the analyzer A is provided with its own pumping component, integral with the analyzer.

It can then be seen that, whatever the initial gas source in question (that is to say the point at which the gas is tapped from the enclosure or enclosures), the tapped gas reaches the collection point R and then the tertiary line $L_T$ at a pressure substantially equal to atmospheric pressure, the analyzer A tapping, via its own pumping component, only the gas flow rate which it needs in order to operate, via the take-off of the line $L_A$ from the tertiary line, the rest of the gas reaching the collection point R and which is not directed to the analyzer being discharged along the tertiary line to the vent E.

The pumps P1, P2, P3, and P are then dimensioned according to the distance between the analysis bay and the tapping points, the pump P being, in particular, dimensioned so that the flow rate reaching the collection point R and therefore the tertiary line $L_T$ is higher than the flow rate which the analyzer A needs (and will pump) in order to operate.

It can thus readily be seen, on inspecting this FIG. 1, that the solenoid valves $V_A$ and $V_P$ in combination make it possible, for example, during pauses or alternatively at night when the installation is offline, to direct a purge gas taken from the line $L_{PR}$, or alternatively a calibration gas taken from the line $L_C$, to the analyzer A, all the tapping lines $L_{Pi}$ then being in such a configuration, either definitively off or flushed but in communication with their associated vents $E_i$.

Figure 3:
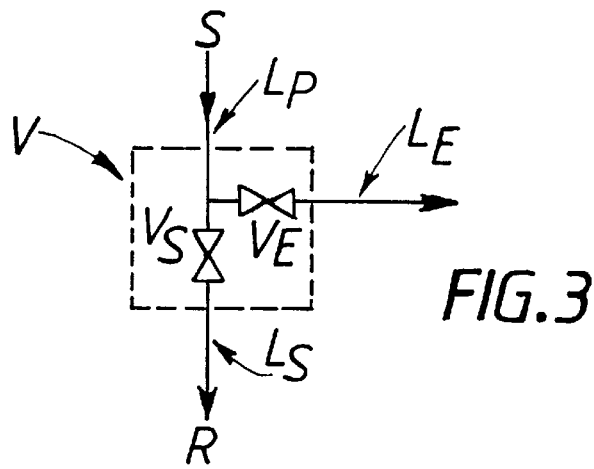
FIG. 3 illustrates an embodiment of a directing component according to the invention, as constituted by the assembly formed by the point of connection of the associated sampling, discharge and secondary lines, each secondary and discharge line being provided with a two-way valve.

Although each directing component in FIG. 1, and in particular the valves $V_i$ of each tapping line, consists of a three-way valve, other types of directing components could of course be conceived of, without departing from the scope of the present invention, as illustrated for example in the embodiment in FIG. 3, where in this case the directing component V consists of the point of connection of the tapping line $L_P$, taken from the source S, of the secondary line $L_S$ which is directed towards the collection point R, and the discharge line $L_E$, each of the lines $L_E$ and $L_S$, being provided, downstream of the point, with a two-way valve (respectively $V_S$ and $V_E$) making it possible to allow or prevent the flow of the gas in each line, and therefore indeed making it possible to direct the gas taken from the initial gas source S in turn, according to requirements, to the collection point R or, alternatively, to the discharge.

Figure 5:
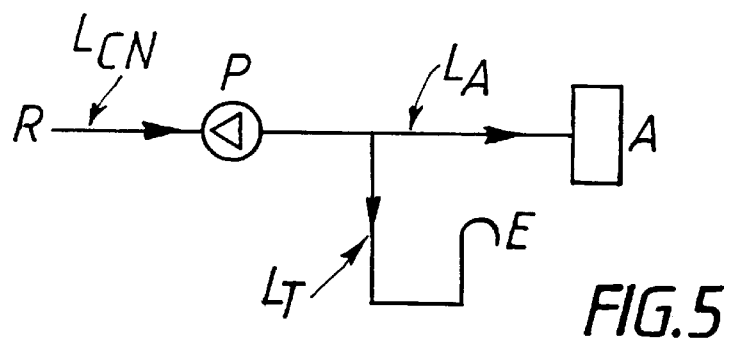

As will be readily apparent to the person skilled in the art, although the installation in FIG. 1 represents an embodiment in which the analysis line $L_A$ is taken off from the tertiary line $L_T$, other configurations may be envisaged, without departing from the scope of the present invention, and should be considered as falling within the general formulation used above in this description, according to which the installation includes "at least one analysis line connected in its upstream part to the tertiary line and in its downstream part . . . ". Thus, the partial representation in FIG. 4 repeats the connection configuration in FIG. 1, while FIG. 5 illustrates a variant which rather would be described by the fact that the tertiary line is taken off from the analysis line $L_A$, the two formulations being interchangeable:

the two lines (analysis and tertiary) are in all cases "connected" (take-off) at one point, and it may be considered that, in the case of FIG. 5 as well, the tertiary line is "connected in its upstream part to the collection point", even though it is through a "connection" line section symbolically represented by $L_{CN}$ a in the figure.

It will therefore be understood that the nomenclature is of only secondary importance, and what should most of all be addressed is the real purpose of each line.

Figure 4:
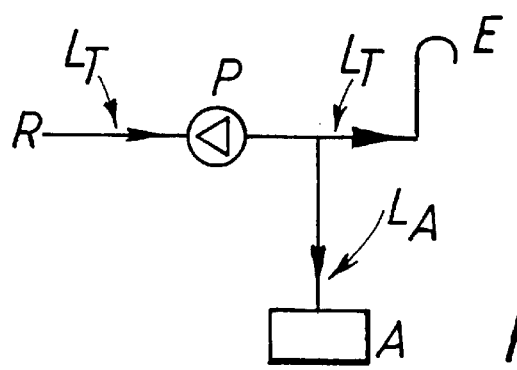
FIGS. 4 and 5 illustrate two alternative embodiments of the invention with the analysis line being taken off from the tertiary line which leads to a vent.

It will be noted however, that the configuration in FIG. 1 and FIG. 4 is advantageous because the gas tapped by the analysis line $L_A$ from the tertiary line $L_T$ will more reliably be at atmospheric pressure since it is being directed towards the vent E.

Figure 6:
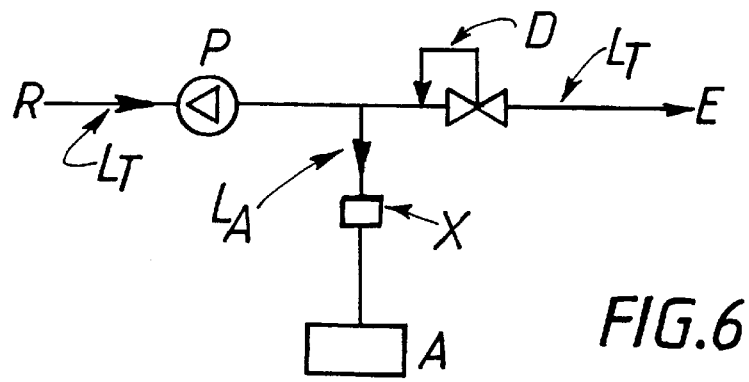
FIG. 6 is a partial representation of an installation according to the invention, the tertiary line comprising an overflow downstream of the point of connection of the analysis line, the analysis line being itself provided with a component for creating a pressure head loss.

Returning now to the detailed description of FIG. 1, although an application example was envisaged above in which the analyzer A was provided with its own pumping component, it is of course also possible to envisage an analyzer A which does not have its own pumping component, in which case it is advantageous to adopt according to the invention the configuration schematically represented in the scope of FIG. 6, in which the tertiary line $L_T$ includes an overflow D downstream of the point of connection of the analysis line $L_A$ to the tertiary line, while the analysis line $L_A$ is itself provided with a component X for creating a pressure head loss.

This component for creating a pressure head loss may be formed in a wide variety of ways from a component such as a throttling valve, or alternatively a shut-off valve, a flow limiter, a calibrated orifice, or, alternatively, in a very general way, this means for creating a pressure head loss may also be obtained by a particular configuration of the pipelines used at this location on the line.

It can therefore be seen that the assembly consisting of the overflow in the tertiary line (an overflow being considered as an upstream pressure regulator) and the component for creating a pressure head loss in the analysis line will make it possible to ensure that there is a constant flow rate in the analysis line and therefore reach the analyzer, irrespective of the tapping point in question, and the pressure of the gas in the tapping line in question, since the pressure in the tertiary line and in the analysis line is fully fixed regardless of the variations which may take place upstream.

The same comment as made above about whether to regard the analysis line as being taken off from the tertiary line or the tertiary line as being taken off from the analysis line could be made again here.

Figure 2:
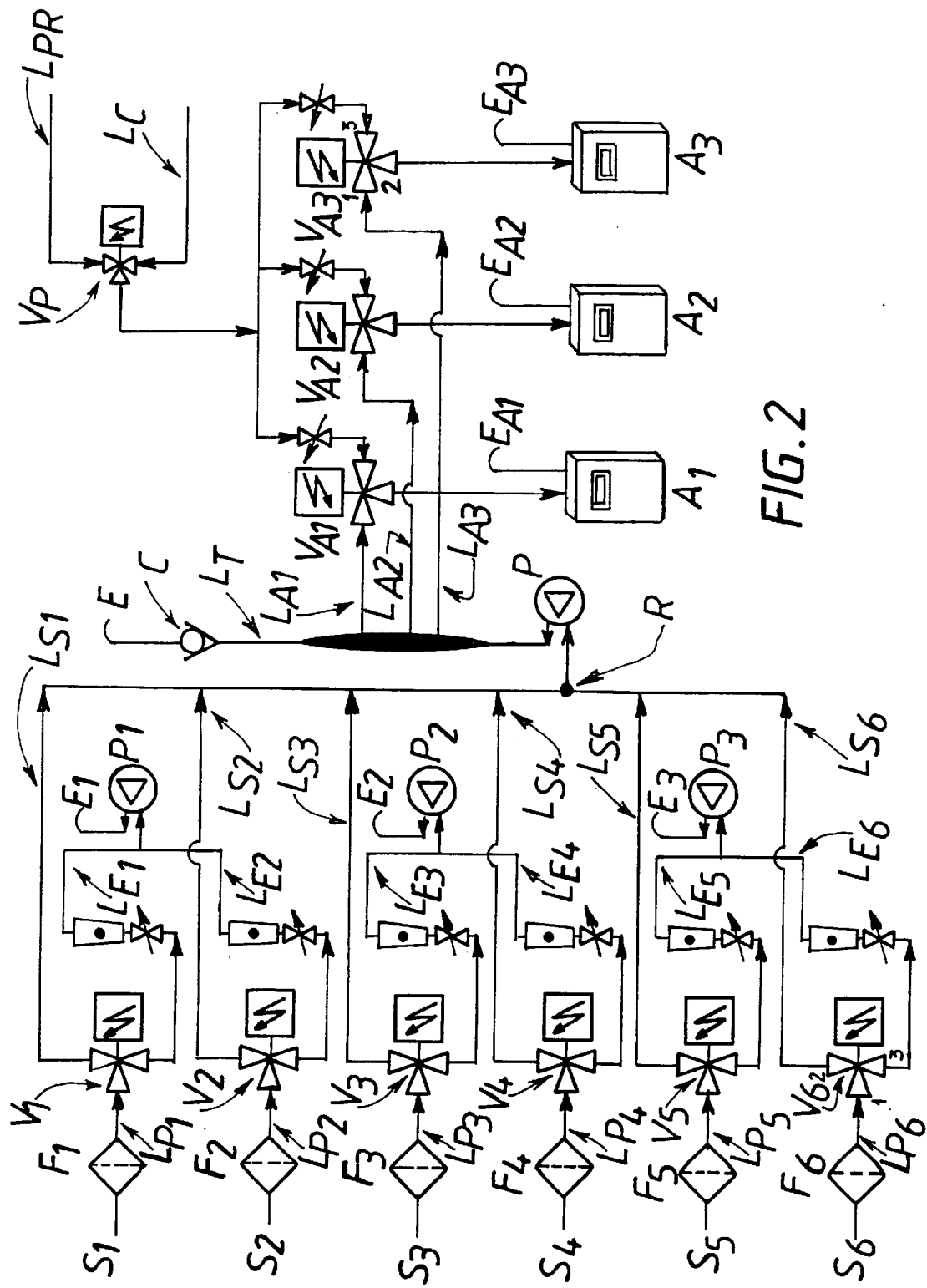
FIG. 2 is a schematic representation of an installation according to the invention, including three analyzers and three analysis lines, which are connected to the tertiary line at a feed tank.

While FIG. 1 illustrates an analysis installation according to the invention which includes a single analyser A, FIG. 2 illustrates, for its part, an analysis installation according to the invention which includes three analyzers, $A_1$, $A_2$, and $A_3$.

The installation in FIG. 2, upstream of the collection point R, is then unchanged compared with the installation in FIG. 1, and for this reason the description below will only deal with the section downstream of the collection point R.

The installation here includes one analysis line per analyzer (respectively $L_{A1}$, $L_{A2}$, and $L_{A3}$,) each analysis line being connected to the tertiary line $L_T$ at a feed tank, represented on the tertiary line by a dark oblong shape.

Each analysis line furthermore includes a directing component, here consisting of three-way solenoid valve ($V_{A1}$, $V_{A2}$, and $V_{A3}$)

As before, each analyzer is here again provided with a gas discharge allowing the received gas to be discharged to a vent, respectively $E_{A1}$, $E_{A2}$, and $E_{A3}$.

It can furthermore be seen that the installation has a solenoid valve $V_P$, which is connected to each solenoid valve $V_{Ai}$ and can direct a purging gas (taken from the line $L_{PR}$) or a calibration gas (taken from the calibration line $L_C$) to each solenoid valve $V_{Ai}$ and therefore to each analyzer.

It can therefore be seen that an installation of this type makes it possible to analyze one or more components for each tapping point, while maintaining all the advantages already indicated in the scope of FIG. 1, linked with the continuous tapping of the various analyzed points upstream of the collection point R.

The variants already described in the scope of FIGS. 3 to 6 could of course also be adopted in the scope of this installation in FIG. 2 (directing component consisting of a T and two two-way valves, or, alternatively, analyzers not provided with their own pumping component and fed through a component for creating a pressure head drop).

Here again, the three ways of the solenoid valve $V_{A3}$ have been numbered 1, 2, and 3 so as to give a clearer explanation of the way in which this solenoid valve and, in general, the installation operate.

When the coil of the solenoid valve $V_{A3}$ is on, the passage 1-2 is employed, while when the coil of the solenoid valve $V_{A3}$ is not on, it is the passage 1-3 which is employed.

Let us now consider the example of a case in which the gas taken from the source S6 is directed to the collection point R, all the other samples taken from the other sources $S_1$ to $S_5$ being directed to their respective vent E1 to E3.

If the gas taken from $S_6$ is to be analyzed, for example, by the analyzer $A_3$, the coil of the solenoid valve $V_{A3}$ is then turned on (by an auxiliary control system which will not be described here, these being control systems already mentioned with which the person skilled in the art of analysis and process control is very familiar), allowing the gas to flow along the passage 1-2, while the other solenoid valves $V_{A1}$ and $V_{A2}$ are not on, allowing the analyzers $A_1$ and $A_2$ to be flushed with the purging gas taken from the assembly $V_P/L_{PR}$.

Of course, if a gas sample taken from the source $S_6$ were then also to be analyzed by another of the analyzers $A_1$ or $A_2$, it would then be perfectly possible to turn the coil of the solenoid valve $V_{A3}$ off, in order to allow the analyzer $A_3$ to be purged with purging gas, and to turn on the coil of, for example, the solenoid valve $V_{A2}$ in order to allow the gas sample taken from the source $S_6$ to reach the analyzer $A_2$, the solenoid valve $V_{A1}$, then remaining off, and the analyzer $A_1$ being purged.

What is claimed is:

1. Installation for analyzing the level of at least one element, from at least two initial gas sources comprising:
    at least two sources of initial gases to be analyzed;
    at least two tapping lines, each line being connected in an upstream part thereof to one of said initial gas sources, and in a downstream part thereof to a respective flow-directing component;
    at least two discharge lines, each discharge line being connected in an upstream part thereof to one of said directing components and in a downstream part thereof to a discharge or to a storage point;
    at least two secondary lines, each secondary line being connected in an upstream part thereof to one of said directing components and in a downstream part thereof to a collection point,
    wherein each directing component is capable of directing a sample from the initial gas source which is associated with the directing component to the respective discharge line associated with the directing component or to the collection point via the respective secondary line associated with the directing component;
    a tertiary line, connected in an upstream part thereof to the collection point and in a downstream part thereof to a discharge or to a storage point; and
    at least one analysis line, connected in an upstream part thereof to the tertiary line and in a downstream part thereof to at least one analyzer.

2. Installation according to claim 1, wherein the tertiary line comprises a pumping component located between the collection point and the point of connection between the tertiary line and said at least one analysis line.

3. Installation according to claim 1, wherein the tertiary line comprises a non-return valve downstream of the point of connection of said at least one analysis line to the tertiary line.

4. Installation according to claim 1, wherein the tertiary line comprises an overflow downstream of the point of connection of said at least one analysis line to the tertiary line, and at least one of the analysis lines comprises a component for creating a pressure head loss.

5. Installation according to claim 1, wherein the discharge line or at least one of the discharge lines comprises a pumping component (P).

6. Installation according to claim 1, wherein the or each analysis line comprises a directing component which is capable of directing a calibration gas or a purging gas to the at least one analyzer of the gas to be analyzed.

7. Installation according to claim 1, wherein said directing component or components comprise a three-way solenoid valve.

8. Installation according to claim 1, wherein said directing component or components of the tapping lines comprise an assembly formed by the point of connection of the associated tapping, discharge and secondary lines, each secondary and discharge line comprising, downstream of the point of connection, a component capable of allowing or interrupting the flow of gas through the line in question.

9. Installation according to claim 1, wherein said initial gas sources are at a pressure above atmospheric pressure.

10. Installation according to claim 9, wherein said initial gas sources are analysis take-offs from a gas distribution network.

11. Installation according to claim 1, wherein said initial sources are at a pressure substantially equal to atmospheric pressure or below atmospheric pressure.

12. Installation according to claim 11, wherein said initial gas sources are analysis take-offs from various points of an enclosure employing a gas atmosphere.

13. Installation according to claim 1, further comprising a plurality of analyzers, wherein the analysis line or lines are connected to the tertiary line at a feed tank.

14. Installation according to claim 13, further comprising a single analysis line connecting the tertiary line and the analyzers arranged in series.

15. Installation according to claim 13, further comprising one analysis line per analyzer.

* * * * *